United States Patent [19]

Grill

[11] Patent Number: 5,258,922
[45] Date of Patent: Nov. 2, 1993

[54] PROCESS AND DEVICE FOR DETERMINING OF SURFACE STRUCTURES

[75] Inventor: Wolfgang Grill, Königstein, Fed. Rep. of Germany

[73] Assignee: Wieslaw Bicz, Frankfurt am Main, Fed. Rep. of Germany

[21] Appl. No.: 922,647

[22] Filed: Jul. 30, 1992

Related U.S. Application Data

[63] Continuation of Ser. No. 536,900, Jun. 12, 1990, abandoned.

Foreign Application Priority Data

Jun. 12, 1989 [DE] Fed. Rep. of Germany ....... 3919159
May 18, 1990 [DE] Fed. Rep. of Germany ....... 4016105

[51] Int. Cl.$^5$ .................... G06K 9/00; G01N 29/00
[52] U.S. Cl. .................... 364/506; 364/576; 364/413.25; 73/602; 382/4
[58] Field of Search .............. 364/506–508, 364/576, 413.25; 340/825.34; 73/599–602, 620, 632; 382/1, 2, 4, 5; 356/71; 359/901; 367/99; 128/653.1, 660.01, 660.07, 660.09

[56] References Cited

U.S. PATENT DOCUMENTS

| | | | |
|---|---|---|---|
| 3,805,596 | 4/1974 | Klahr | 73/602 |
| 4,094,306 | 6/1978 | Kossoff | 128/661.01 X |
| 4,107,775 | 8/1978 | Ott | 364/576 |
| 4,167,180 | 9/1979 | Kossoff | 128/660.09 |
| 4,213,183 | 7/1980 | Barron et al. | 364/507 |
| 4,631,965 | 12/1986 | DeVadder et al. | 73/602 |
| 4,662,222 | 5/1987 | Johnson | 73/602 |
| 4,794,546 | 12/1988 | Nicolas | 364/507 |
| 4,817,015 | 3/1989 | Insana et al. | 364/507 |
| 4,817,016 | 3/1989 | Thompson et al. | 364/507 |
| 4,866,614 | 9/1989 | Tam | 364/507 X |
| 4,873,984 | 10/1989 | Hunt et al. | 73/602 X |
| 4,876,725 | 10/1989 | Tomko | 382/4 |
| 4,881,549 | 11/1989 | Rhyne | 73/602 X |
| 4,933,976 | 6/1990 | Fishbine et al. | 382/4 |
| 4,977,601 | 12/1990 | Bicz | 382/4 |
| 4,995,086 | 2/1991 | Lilley et al. | 340/825.34 X |
| 5,029,475 | 7/1991 | Kikuchi et al. | 73/602 |
| 5,062,297 | 5/1991 | Hashimoto et al. | 73/602 X |

Primary Examiner—Thomas G. Black
Assistant Examiner—Thomas S. Auchterlonie
Attorney, Agent, or Firm—Herbert Dubno

[57] ABSTRACT

A method and device for determining surface structure and subsurface structures wherein the article to be examined is placed upon a support surface and through a liquid or solid medium ultrasonic waves are directed at the surface and backscattered waves are received and processed. The frequency of the ultrasonic waves is selected to provide information of the subsurface structure to a depth of substantially one wavelength.

12 Claims, 3 Drawing Sheets

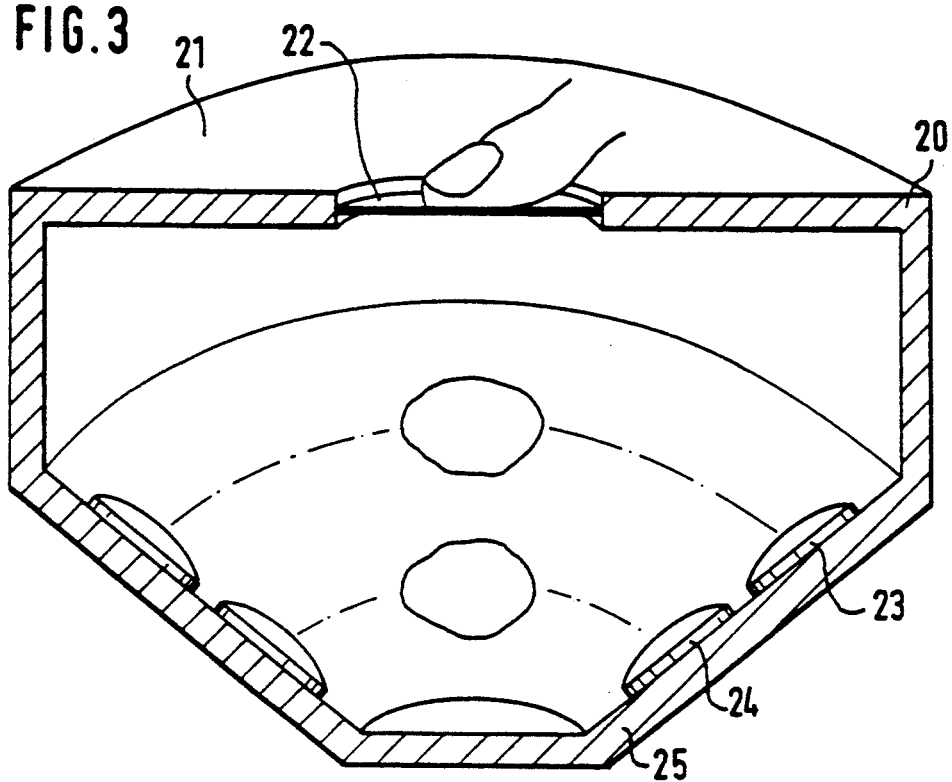
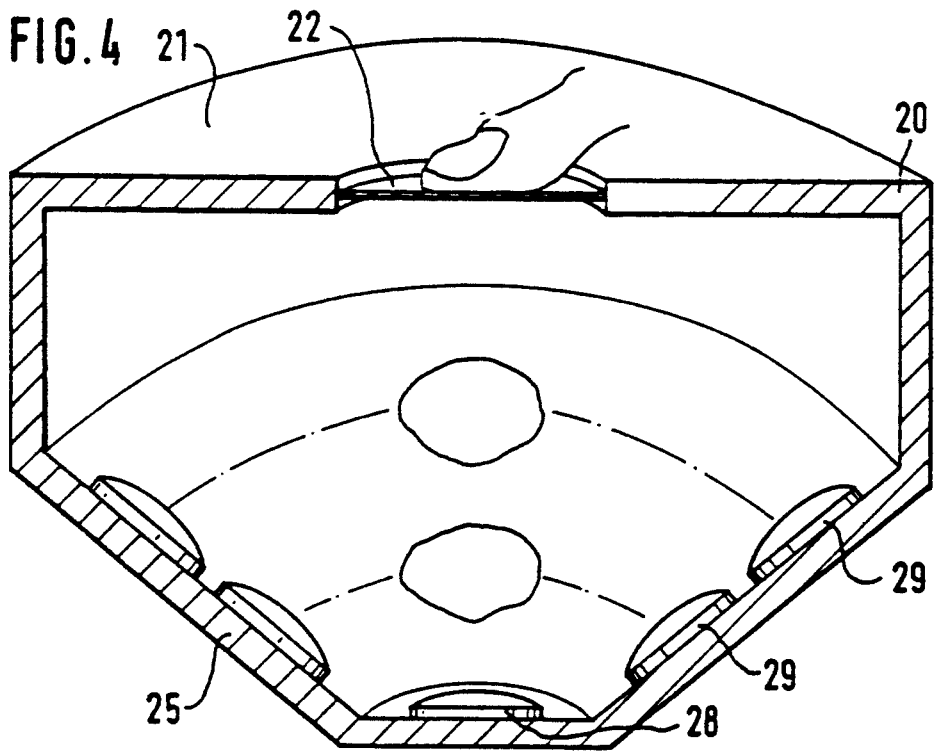

PROCESS AND DEVICE FOR DETERMINING OF SURFACE STRUCTURES

This is a continuation of co-pending application Ser. No. 07/536,900 filed on Jun. 12, 1990, now abandoned.

FIELD OF THE INVENTION

The present invention relates to a process and a device for determining of surface structures and also of surface-adjacent structures of items.

BACKGROUND OF THE INVENTION

Conventional optical processes only permit a determination of the surface condition rather than the determination of the structures closely underneath the surface, i.e. subsurface structures. Such determination may result in faulty analyses, as the surface structure is easily exposed to external influences, both desired and undesired. Meaningful determinations of such identification, hence, structures, therefore, cannot be carried out any longer after changes in the surface. To overcome the afore-described disadvantage of the state-of-the-art capabilities of determining the texture of surfaces, it is desirable to the invention encounters the problem of determine not only the surface texture but also, at the same time, the also the structure below the surface down substructure to a depth of about one wavelength.

OBJECT OF THE INVENTION

It is, therefore, an object of the invention to provide an improved method and device for determining surface structures and such subsurface structures.

SUMMARY OF THE INVENTION

The invention provides the following process for determining the texture of the surface and the closedly adjoining subsurface structure of items. In the practice of the invention, the item disposed on a planar or arcuate face, through a solid body or a body filled with fluid, is exposed to ultrasonic waves, and the waves back-scattered and reflected on the item through such exposure are taken up by a receiver, with the wavelengths of the ultrasonic waves being adjusted to the structure of the item.

Thanks to the intensity of the back-scattered and reflected waves the texture of the surface and of the subsurface structure down to approximately one wavelength, can be determined because the scatter and reflection are influenced by the non-uniform density of the structure, with the influence exerted by the subsurface structure being dependent on the wavelength. The wavelengths of the ultrasonic waves, in the practice of the invention, are, therefore, so selected that they approximately correspond to or are up to 10 times shorter than the minimum or maximum cycle duration resulting from the spatial frequency spectrum of the item. The spatial frequency spectrum of each item is defined thereby by means of frequencies and is computed by Fourier analysis. The internal structure of the surface of the item to be examined is a phase and/or amplitude structure. The phase structure, causing a time displacement of the wave, results in an unsymmetrical back-scattering.

The transmitter of the ultrasonic waves and the receiver of the scattered and reflected waves may be disposed separately from one another. However, also a single ultrasonic transducer may be employed, because the reciprocity of a large variety of conversion effects, allows ultrasonic transducers to be used both as transmitters and receivers. The types of ultrasonic transducers selected are those that transmit planar or spherical waves or waveforms differing only in minor respects therefrom. Disc-type transmitters and receivers have proved to be particularly advantageous. The latter-mentioned transmitters can be made of piezo-ceramics. Transmitters of this type transmit wavefronts which lie parallel to the surface of the transmitter, and the receiver only responds to such waves the fronts of which extend in parallel to the surface thereof.

The receiver, in this manner, directly receives a Fourier transformation based on the propagation of the waves. The Fourier transformation conveys any parameter, such as phase, amplitude or intensity. Depending on the structure of the item to be investigated, for example, of a finger-tip, of a piece of fabric etc., scatter and intensity of the back-scattered waves into the various directions, vary in strength. Units of measurement, such as numerals, colors and other reference characters can be associated with the individual values of intensity. With the aid of such an association, in the evaluation of the back-scattered waves, pictures are obtained that are easily comparable. It is especially with the association of a colors scale to the varying values of intensity, that images can be generated mirroring quite impressively the item investigated.

It has been shown that the afore-described types of waves are the optimum ones although it should be noted that the waves also can be differently shaped. Such differently shaped waves can be generated by correspondingly configured transducers or lenses. For example, it is also possible to use a cylindrical shape of the waves, or to use waves having two radii of curvature perpendicular to one another.

The transmitter and the receiver or the ultrasonic transducer in general converting or reversing waves into signals, can be movably disposed and can scan the item for predetermined or for all angles, thereby providing information in each position of the transducer, through the varying scatter and reflection, with the multiplicity of items of information insuring a very precise picture of the surface texture and of the structure close to the surface. Also, it is possible to provide a plurality of stationarily mounted transmitters and receivers or ultrasonic transducers furnished with planar or arcuate surfaces. Piezo ceramics has proved to be a material suitable for transmitters, receivers or transducers.

The transmitter or transducer either may continuously transmit waves to the item or may simply transmit wave pulses. In the latter instance, the transmitter is controlled by a pulse generator.

According to the process of the invention, the structure of the surface and the structure close to the surface can be investigated and the properties can be stored in the form of information data. Such information data can be compared with other data stored or, with the aid of the methods of the Fourier analysis, can be graphically shown through reconstruction. In the process according to the invention, the transmitter or transducer is excited by a frequency generator through a switch and, optionally, through an amplifier. In the event that only wave pulses are to be provided to the item, the aforementioned switch is pulse-controlled. The waves reflected or scattered by the item will be taken up by the receiver or transducer putting the information data regarding the intensity and/or phase of the back-scatter and reflection, via a detector—optionally via an amplifier—and a time control optionally coordinated with the pulse generator, into a computer for being analyzed and recorded.

The afore-described process is especially suitable for the examination of items, such as finger-tips, documents, cards etc. The process enables, for the first time, not only to determine the mere surface texture but also the structures close to the surface through penetration of the ultrasonic waves, thereby substantially improving and also simplifying the identification of the material investigated. Through comparing with previously recorded structures and surface conditions it is possible with the aid of few data, to identify the structure to be investigated and to exclude falsifications which, for example, in the determination of the surface texture and the structures close to the surface of finger-tips, results in that the amount of data needed for comparing purposes can be substantially reduced to as low as 30 bytes. In addition, the time needed for conventional comparing purposes, can be saved. Moreover, the process according to the invention is independent of displacements, provided that the wave is planar, eliminating the need of positioning the item. It is only the turning of the structure that may have to be compensated.

Through determination of the density differences according to the process of the invention, a falsification of the structure of the item to be investigated will be rendered substantially difficult—if not impossible—as it is substantially more difficult to manipulate density differences of structures than surface structures.

BRIEF DESCRIPTION OF THE DRAWING

The drawings illustrate embodiment of devices for carrying into effect the afore-described process. In the drawing:

FIG. 3 is a section similar to FIG. 1 in which shows a modified design; and

FIG. 4 is a cross sectional view which shows another modification.

SPECIFIC DESCRIPTION

Figure 1:
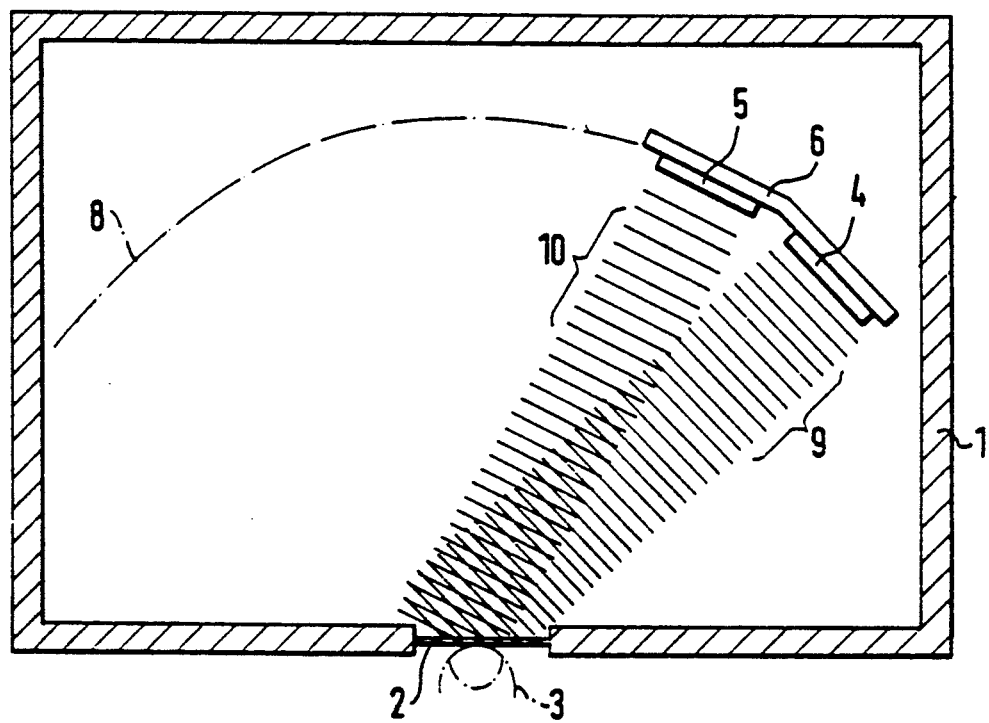
FIG. 1 is a cross sectional view which schematically shows the construction of a device for carrying out the process of the invention.

Referring to the drawing, FIG. 1 schematically show a device for carrying out the afore-described process intended to determine surface structures and structures close to the surface. The device comprises a closed box 1 filled with a liquid fluid, such as water. The bottom side of the box has a support face 2 against which is forced the object to be investigated and to be analyzed. The support face 2 is made, for example, of plastic material.

As the process of the invention is suitable for the determination of fingerprints, the object shown in the example of embodiment is a finger-tip 3. Any other objects, such as crystalline plates, ancient scripts, textile materials etc., can, of course, be identified. Located in box 1 are transmitter 4 and receiver 5 both of disc-type configuration and made of identical material, preferably of piezo ceramics. Receiver and transmitter are disposed in side-by-side relationship on a common carrier 6 moving along a curved trajectory 8 within box 1. For that purpose, carrier 6 is guided in accordance with the trajectory of movement and is actuated through an engine. Carrier 6 is shaped to correspond to the curve of movement. The set of wave fronts transmitted by transmitter 4 and extending in parallel are designated by numeral 9 while the wave fronts scattered back to the receiver are designated by numeral 10. The carrier moves along the trajectory 8, hence, covering the finger-tip 3 circumferentially, thereby determining the spatial frequency spectrum thereof. A finger-print is comparable to the structure of a grid (lines extending in parallel) as the print only consists of lines extending in lumps in various directions, and as, in grid structures, substantially only one frequency occurs. A finger-tip, transformed into a frequency spectrum, results in a rather simple structure which at least is substantially simpler than the fingerprint.

Figure 2:
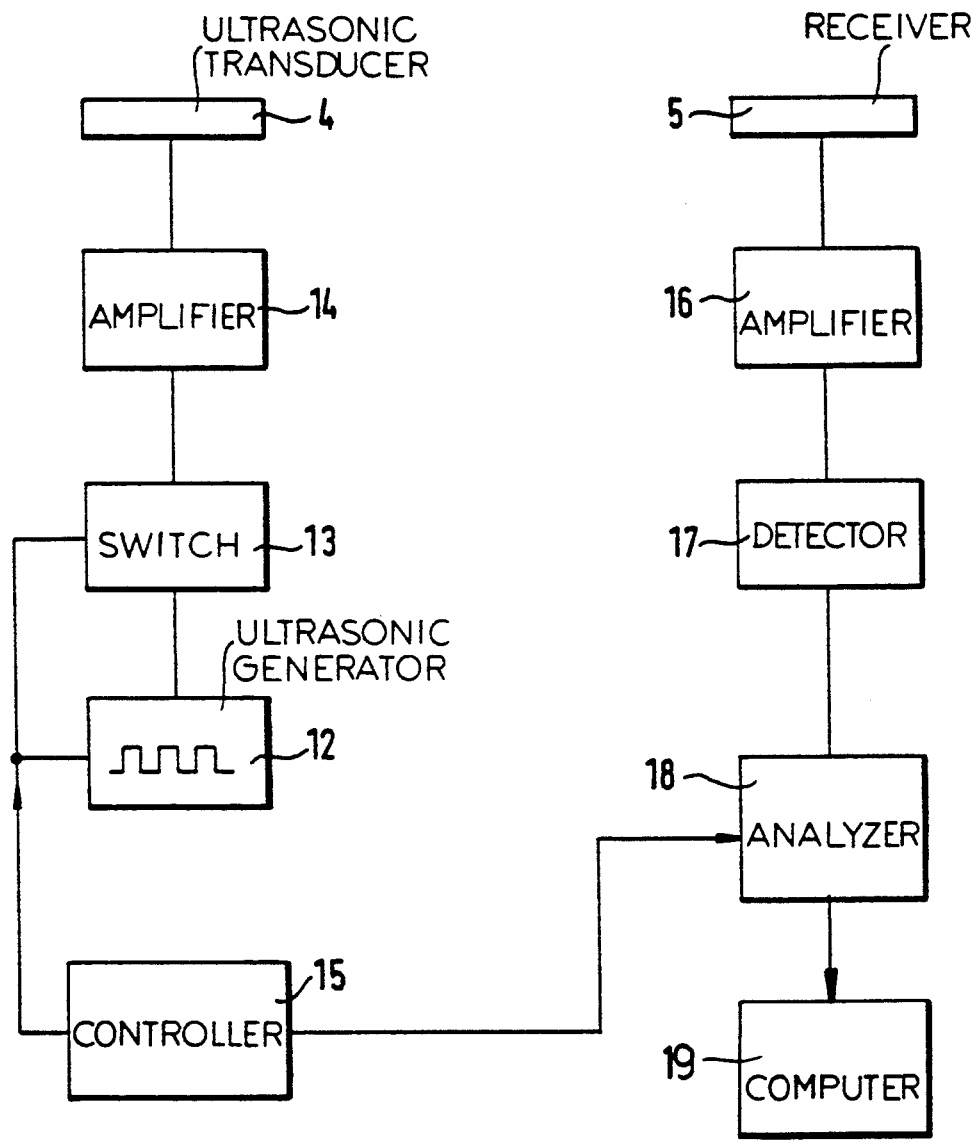
FIG. 2 is a block diagram which shows a circuit arrangement for the device of FIG. 1.

FIG. 2 shows a suitable circuit which, on the one hand, generates the ultrasonic waves and, on the other hand, analyzes the back-scattered waves and performs a coordination in time. An ultrasonic generator 12, through a switch 13 and an amplifier 14, energizes transmitter 4. The control system 15 coordinates the proper time succession of the signals. The signals taken up by the receiver 5, through an amplifier 16, are fed to a detector 17 and the analyzer 18 coupled to the control system 15. The system 18 passes on the digital information of the signals determined to a computer 19.

FIG. 3 shows a modified system for carrying into effect the process of the invention, wherein the closed box 20, on the top side 21 thereof, exhibits the mounting surface 22. The box 20 is of a circular cross-section, and transmitters 23 and receivers 24 circularly are disposed on bottom portions 25 obliquely extending toward the center. The box 20, optionally, may be filled with a solid or liquid fluid. Filling of the box with a liquid or solid substance is imperative for attenuating the sonic waves.

Transmitter 23 and receiver 24, through the circuit of the type as shown in FIG. 2, are inter-connected. The individual transmitters and receivers are connected in series and coordinated in time. The embodiment according to FIG. 4 distinguishes from that of FIG. 3 only in that the transmitter 28 is located in the bottom center while the receivers 29 are disposed along two circles on the inclined bottom portions.

The surface texture and the structures near the surface can be reliably identified by means of the afore-described systems. The selection of the system respectively is dependent on the item and the degree of the required accuracy.

I claim:
1. A process for determining characteristics of a surface structure and a subsurface structure adjacent said surface structure of an object, comprising the steps of:
   (a) placing said object upon a surface on one side of a layer;
   (b) providing body of a liquid or solid wave transmitting medium against a surface on an opposite side of said layer;
   (c) directing ultrasonic waves through said medium and said layer against said object whereby ultrasonic waves are backscattered from said object into said medium and reflected from said object into said medium;
   (d) positioning an ultrasonic receiver in said medium to receive directly ultrasonic waves backscattered from said object into said medium;
   (e) receiving at said receiver and analyzing ultrasonic waves backscattered through said medium from said object by Fourier analysis of intensity of the ultrasonic waves measured to determine characteristics of the surface of said object and subsurface structures thereof; and (f) controlling wavelengths of the ultrasonic waves transmitted through said medium to said object in accordance with said structure of said surface and said subsurface structure.

2. The process defined in claim 1 wherein said wavelengths of said ultrasonic waves are selected to correspond to at most one-tenth of a maximum cycle length of a spatial frequency spectrum for said object.

3. The process defined in claim 1 wherein said ultrasonic waves are emitted from and received by a single ultrasonic transducer.

4. The process defined in claim 1 wherein said ultrasonic waves are directed through said medium toward said object with a wavefront selected from the group which consists of planar, spherical and cylindrical wavefronts.

5. The process defined in claim 1 wherein said object is subjected to the ultrasonic waves simultaneously over an entire surface in contact with said layer.

6. The process defined in claim 1 wherein said object is subjected to ultrasonic waves from at least one stationary transmitter and backscattered ultrasonic waves are picked up by at least one stationary ultrasonic receiver.

7. An apparatus for determining characteristics of surface structures and subsurface structures of an object comprising:

(a) a housing filed with a liquid or solid wave transmitting medium, said housing being formed with a layer having a surface on one side of said layer in contact with said medium and a surface outside of said housing against which an object can be placed;

(b) a disk-shaped transmitter of ultrasonic waves in said housing for transmitting ultrasonic waves through said medium to said layer and against said object whereby ultrasonic waves characterizing surface structures of said object and subsurface structures thereof are backscattered and reflected into said medium from said object;

(c) at least one disk-shaped receiver in said housing receiving said backscattered ultrasonic waves;

(d) means for analyzing the received backscattered ultrasonic wave intensity for determining by Fourier analysis said characteristics of said surface structure and said subsurface structure of said object; and (e) means for controlling the frequency of the ultrasonic waves in accordance with the subsurface structures.

8. The apparatus defined in claim 7 wherein at least one transmitter and at least one receiver are mounted on a support in said housing displaceable along an arcuate trajectory opposite said layer.

9. The apparatus defined in claim 7 wherein a plurality of receivers are disposed in two concentric circles in said housing.

10. The apparatus defined in claim 7 wherein a plurality of ultrasonic transmitters and a plurality of ultrasonic receivers are provided in concentric circles on a wall of said housing opposite said layer.

11. The apparatus defined in claim 7, further comprising an ultrasonic generator, a switch connected to said ultrasonic generator and controlled by a pulse generator, an amplifier connected to said switch and feeding said transmitter, said means for analyzing including an amplifier connected to said receiver, a detector connected to said amplifier, an analyzer circuit controlled by a controller simultaneously controlling said generator and said switch and a computer receiving an output from said analyzer circuit.

12. The apparatus defined in claim 7 which comprises a frequency generator which through a switch controlled by a pulse generator, and an amplifier excites a transmitting transducer exposing the object to ultrasonic wave packages, so that waves reflected and scattered by the object are taken up by a receiving transducer putting information on the intensity and phase of backscatter, through a rectifier, through an amplifier, and a time control coordinated with the pulse generator, into a computer for analyzing and recording.

* * * * *